(12) United States Patent
Russo et al.

(10) Patent No.: US 6,410,703 B1
(45) Date of Patent: Jun. 25, 2002

(54) IDENTIFICATION OF A VACCINE CANDIDATE FROM AN EXTRAINTESTINAL ISOLATE OF *E. COLI*

(75) Inventors: Thomas Russo, Amherst; Ulrike Carlino, Buffalo, both of NY (US)

(73) Assignee: The Research Foundation of the State University of New York, Amherst, NY (US)

( * ) Notice: Subject to any disclaimer, the term of this patent is extended or adjusted under 35 U.S.C. 154(b) by 0 days.

(21) Appl. No.: 09/668,113

(22) Filed: Sep. 22, 2000

Related U.S. Application Data

(60) Provisional application No. 60/155,621, filed on Sep. 22, 1999.

(51) Int. Cl.$^7$ .................. C07H 21/02; C12R 21/06; C12R 21/04

(52) U.S. Cl. .................. 536/23.1; 435/69.1; 435/71.1; 435/252.1; 435/252.3; 435/252.8

(58) Field of Search ................ 435/69.1, 71.1, 435/252.1, 252.3, 252.8; 536/23.1

(56) References Cited

PUBLICATIONS

Baumler et al, Journal of Bacteriology, Mar. 1998, pp. 1446–1453.*

Johnson et al, Molecular Epidemiological and Phylogenetic Associations of Two Novel Putative Virulence Genes, iha and iroN E. coli' among *Escherichia coli* Isolates from Patients with Urospsis.; Infect. Immun. May 2000, vol. 68, No. 5, pp. 3040–3047.

Russo et al, Identification, Genomic Organization, and Analysis of the Group III Capsular Polysaccharide Genes kpsD, kpsT, and kpsE from an Extraintestinal Isolate of *Escherichia coli* (CP9, 04/K54/H5). J. Bacteriology, Jan. 1998, vol. 180, No. 2, pp. 338–349.

Russo et al, Identification of Genes in an Extraintestinal Isolate of *Escherichia coli* with Increased Expression after Exposure to Human Urine, Infect. Immun. Oct. 1999, vol. 67, No. 10, pp. 5306–5314.

* cited by examiner

*Primary Examiner*—Lynette R. F. Smith
*Assistant Examiner*—Vanessa L Ford
(74) *Attorney, Agent, or Firm*—Hodgson Russ LLP

(57) ABSTRACT

The present invention is directed to identifying a gene, iroN$_{ec}$, from an extraintestinal isolate of *E. coli*, CP9. This gene was identified from CP9 by screening a library of 527 mutant derivatives of CP9 with active TnphoA fusion in human urine. Two mutant derivative CP9.45 and CP9.82 possessed increased PhoA activity in urine due to the TnphoA insertion into iroN$_{ec}$. The product of this gene is an extracytoplasmic protein of 725 amino acids and can be used as vaccine against extraintestinal *E. coli* infections.

6 Claims, 3 Drawing Sheets

US 6,410,703 B1

IDENTIFICATION OF A VACCINE CANDIDATE FROM AN EXTRAINTESTINAL ISOLATE OF E. COLI

This application claims the priority of U.S. provisional application serial No. 60/155,621 filed on Sep. 22, 1999.

FIELD OF THE INVENTION

This invention relates generally to the field of vaccines for bacterial infections. More particularly, this invention identifies a gene that is expressed in extraintestinal isolates of *Escherichia coli* (*E. coli*), and can be used as an immunogen in vaccine formulations.

BACKGROUND OF THE INVENTION

*E. coli* is part of the normal intestinal flora where it does not cause infections. However, infections can occur if the bacteria gain entrance to other tissues and organs. This group of *E. coli* strains has been designated herein as extraintestinal pathogenic *Escherichia coli* (ExPEC). Extraintestinal infections (EIs) due to *E. coli* are common in all age groups and can involve nearly any organ or anatomical site. Typical EIs include urinary tract infection (UTI), meningitis (mainly in neonates and following neurosurgery), diverse intra-abdominal infection, pneumonia (particularly in hospitalized and institutionalized patients), intra-vascular device infection, osteomyelitis, and soft tissue infection, which usually occurs in the setting of tissue compromise. Bacteremia can accompany infection at any of these sites.

Extraintestinal isolates of *E. coli* are responsible for the majority of urinary tract infections (UTI). Eighty to ninety percent of ambulatory UTI, 73% in individuals over 50, and 25% of nosocomial UTI are due to extraintestinal strains of *E. coli*. Uncomplicated urethritis or cystitis occurs most commonly. However, more severe sequelae of UTI includes pyelonephritis, intrarenal and perinephric abscess, and bacterimia with or without septic shock. Thus, it is clear that despite effective antimicrobial therapy, UTI due to *E. coli* causes considerable morbidity and mortality.

Although *E. coli* is considered to be a community-acquired pathogen, it also is the most frequently isolated gram-negative bacillus in long-term care facilities and hospitals. Severe illness and death can occur in otherwise healthy hosts, but adverse outcomes are considerably more likely in the presence of comorbid disease and impaired host defenses.

The scope and magnitude of infection caused by extraintestinal strains of *E. coli* is as great as any invasive bacterial pathogen. In fact, perhaps because disease due to extraintestinal isolates of *E. coli* is so common, the virulence and morbidity of this organism is often overlooked. As a result, extraintestinal strains of *E. coli* continue to be low profile "silent killers" imposing a medical-economic strain on the health care system.

Currently, no effective vaccine is available against ExPEC. To date, efforts to identify specific vaccine candidates against ExPEC have concentrated on virulence traits such as capsule, LPS, and pili. These studies have demonstrated that antibodies directed against these structures confer protection against homologous strains in vivo. However, the inherent marked antigenic variability of these components may limit their utility as vaccine candidates. Thus, there is an ongoing need for identification of novel effective strategies for the prevention and treatment of ExPEC infections including UTI.

SUMMARY OF THE INVENTION

The present invention is directed to identifying a gene, iroN$_{ec}$, from an extraintestinal isolate of *E. coli*. This gene was identified by transposon mutagenesis. TnphoA mutagenesis was performed on the wild type isolate of *E. coli*, CP9, and a library of 527 mutants with active TnphoA fusions was generated and saved. This library was subsequently screened for mutant derivatives with increased PhoA activity in the presence of urine. By this method, the iroN$_{ec}$ gene was identified which encodes a protein of 725 amino acids. This protein has an extracytoplasmic location. DNA homology data and data demonstrating that its transcription is iron repressed supports its function as a siderophore receptor. High stringency Southern hybridization identified DNA sequences homologous to iroN$_{ec}$ in 80–93% of ExPEC strains.

This protein or antigenic epitopes thereof can be used for inducing an immune response against extraintestinal *E. coli* infections. Data is presented to show that IroN$_{ec}$ is strongly immunogenic (without adjuvant) in mice. Further, antibodies developed against IroN$_{ec}$ were observed to be protective in a mouse intra-peritoneal challenge model. Mice immunized with IroN$_{ec}$ had diminished mortality after intra-peritoneal challenge with the *E. coli* strain CP9. Additionally, there was diminished growth of the challenged strain in the liver and spleen in animals immunized with IroN$_{ec}$ compared to non-immunized controls.

Thus, it is an object of the present invention to identify a gene, designated herein as iroN$_{ec}$ in the extraintestinal isolates of *E. coli* with increased expression in human urine.

It is another object of the present invention to provide a polynucleotide that encodes the protein, IroN$_{ec}$.

It is another object of the present invention to provide polynucleotides that hybridize, preferably under high stringency conditions, with a polynucleotide encoding IroN$_{ec}$.

It is anther object of the present invention to provide peptides that are encoded by iroN$_{ec}$ and other polynucleotides of the present invention.

It is another object of the invention to provide antigenic compositions comprising the peptides or antigenic fragments thereof for the treatment or prevention of extraintestinal infections caused by ExPEC.

DESCRIPTION OF THE PREFERRED EMBODIMENTS

Figure 1:
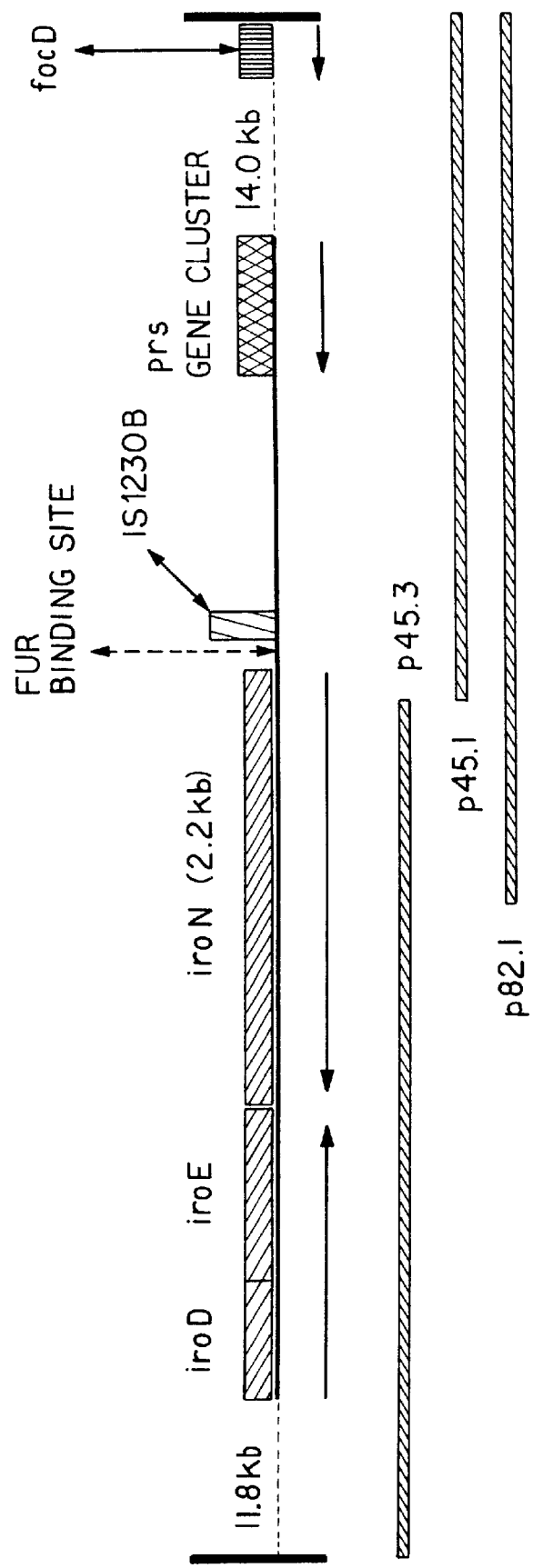
FIG. 1 is a schematic diagram of the iroN$_{ec}$ and the flanking sequence.

The present invention is directed to a gene whose expression is increased in human body fluids such as urine, blood and ascites. This gene, termed iroN$_{ec}$, is represented by the sequence of SEQ ID NO:1.

In one aspect of this invention are provided polynucleotides that are at least 90% identical (homologous) over their entire length to the polynucleotide of SEQ ID NO:1, preferably at least 95% identical, and still more preferably at least 97% identical to the sequence of SEQ ID NO:1, or complementary sequences thereof.

The invention further relates to polynucleotides that hybridize to the sequence of SEQ ID NO:1 under high stringency hybridization conditions. High stringency conditions as used herein means hybridization will occur only if there is at least 90% homology, preferably at least 95% homology, and even more preferably at least 97–99% homology between the sequences. An example of high stringency hybridization conditions is overnight incubation at 42° C. in 50% formamide, 5×SSC, 50 mM sodium phosphate (pH 7.6), 5× Denhardt's solution, 10% dextran sulfate, and 20 μg/ml denatured, sheared salmon sperm DNA. Washing is carried out in 0.1×SSC at about 65° C. Details on the stringent hybridization conditions are well known to those skilled in the art (see Sambrook et al., 1989, Molecular Cloning: A laboratory Manual, Second Edition, Cold Spring Harbor, N.Y.). Another example of high stringency hybridization condition is presented in Example 2.

The polynucleotides of the present invention can be incorporated into vectors which can be used in expression systems for the production of polypeptides. A variety of expression systems are available and known to those skilled in the art.

In another embodiment of the invention are provided peptides that are encoded by the polynucleotides of the present invention. These peptides or antigenic fragments thereof, can be used for diagnostic and immunotherapeutic purposes. "Antigen fragments" are those that are part of the whole protein and are specifically recognized by certain antibodies that also recognize the whole protein and which will generate an immune response that reduces or prevents the incidence or symptoms of $E.\ coli$ infections.

In the present invention, iroN$_{ec}$ was identified by transposon mutagenesis. Transposons or transposable elements are DNA segments that can move in the genome from one site to another. They can also be moved from one bacterium to another by plasmid or other vehicles to be inserted into the host genome. Transposons may be simple or complex. Simple transposons have insertion sequences and no genes other than those involved in their own transposition into the target sequence. Complex transposons contain the insertion elements bracketing additional genes that encode properties such as drug resistance, carbohydrate metabolism, light generation, ice nucleation, and other properties which can function as selectable or screenable markers for the entire transposable elements. Thus, transposons are suitable for the use of identifying and cloning of bacterial genes which are turned off or on in the presence of a particular environment.

The method used for the identification of this gene has been described in Russo et al. (1996, Mol. Microbiology, 22:217–229), the disclosure of which is incorporated herein by reference. A transposon, TnphoA, which is a Tn5 derivative, was used in the present invention. On correct insertion into an open reading frame, this transposon will produce a fusion protein with bacterial alkaline phosphatase (PhoA). Since PhoA is only active when in the periplasm, TnphoA identifies genes whose products are exported across the cell membrane. When a PhoA-specific chromogenic detection reagent (for example, XP; 5-bromo-4-chloro-3-indolyl phosphate) is used, a blue colony is only obtained when TnphoA has inserted into a gene encoding a protein containing the N-terminal export leader peptide sequence.

The pathogen CP9 (Russo et al., 1993, Mol. Microbiol., 9:357–364), an $E.\ coli$ blood isolate cultured from a patient with sepsis, hospitalized at the National Institutes of Health, was used as a model pathogen for identification of genes with increased expression in urine. It is characterized by growth in 80% normal human serum, β-hemolysis, no known antibiotic resistance, O4/K54/H5 serotype, P pilus (class I PapG adhesin), Prs pilus (class III PapG adhesin), type 1 pilus, possession of a 36.2-kb cryptic plasmid (pJEG) and an aerobactin minus genotype. By DNA dot-blot assays, it has also been determined to be sfa, ompT, cnf1 and drb positive (Johnson et al., 1997, Infect. Immun., 65:2153–2159; Russo et al., 1993, Mol. Microbiol., 9:357–364). It is highly virulent in a mouse UTI infection model (Russo et al., 1996, Infec. Immun., 64:2343–2348). Recent studies have established that CP9 is part of a widely disseminated group of uropathogens that are characterized, in part, by possessing group 3 capsules, the O4 specific antigen, and Class 1 and 3 Pap adhesins (Johnson et al., 1997, Infect. Immun., 65:2153–2159; Johnson et al., 1997, Infect. Immun., 65:2153–2159).

All strains of $E.\ coli$ were maintained at −80° C. in 50% Luria-Bertani (L-B) medium and 50% glycerol. L-B broth consisted of 5 grams yeast extract, 10 grams tryptone, 10 grams NaCl per liter (L). Incubations were performed at 37° C. unless otherwise described. For plates, 15 grams of Bacto-Agar (Difco Laboratories Detroit, Mich.) were added per L and kanamycin (kan) (40 μg/mL) or ampicillin (200 μg/ml) (Amresco, Solon, Ohio) were added where appropriate. Urine agar plates were made as described, using pooled urine from 5 healthy donors that did not have a history of having a urinary tract infection (Russo et al., 1996, Mol. Microbiol., 22:217–229).

EXAMPLE 1

This embodiment describes the identification, cloning, and characterization of iroN$_{ec}$.

To identify genes with increased expression in human urine ex vivo that coded for extracytoplasmically located gene products, random TnphoA mutagenesis was performed on CP9. A TnphoA mutant library, consisting of 527 CP9 derivatives containing active TnphoA fusions had been previously constructed (Russo et al., 1993, Mol. Microbiol., 9:357–364) and was used in the present study.

The TnphoA mutant library was screened to identify genes that coded for extra-cytoplasmically located gene products which had increased expression in human urine ex vivo. Transposon mutants were initially plated on human urine agar plates containing kanamycin (40 μg/ml) and 5-bromo-4-chloro-3-indolyl-phosphate-p-toluidine salt (XP), as the colorimetric substrate for an indication of alkaline phosphatase activity. Mutants that appeared to have increased expression via these qualitative screens (as manifested by the relative blue color of the colonies) were confirmed with quantitative assays as follows. For urine and L-B assays quantitative alkaline phosphatase assays were performed as previously described (Russo et al., 1996, supra, Russo et al., 1993, supra). In brief, CP9 and each of its mutant derivatives were grown overnight in L-B broth and human urine. Preliminary experiments established that PhoA expression was the same for CP9 derivatives containing an active PhoA fusion in iroN$_{ec}$ (CP9.45, CP9.82) in log phase and stationary phase grown cells. Cells were then washed, permeabilized, and p-nitrophenyl phosphate was added for detection of alkaline phosphatase activity respectively. To control for both endogenous bacterial alkaline phosphatase activity and any activity from the growth medium (e.g. urine) that may persist despite washing, alkaline phosphatase activity from CP9 was subtracted from the measured activity of its mutant derivatives.

The screening of the TnphoA library resulted in the identification of CP9.45 and CP9.82 (Table 1).

TABLE 1

*E. coli strains and plasmids used in this study*

| Strain/ Plasmid | Genotype or other relevant characteristics | Derivation |
|---|---|---|
| Strains | | |
| CP9 | 04/K54/H5 | clinical blood isolate |
| CP9.45 | iroN$_{ec}$:TnphoA, active TnphoA fusion | Kan$^R$exconjugant of CP9/pRT291 x MM294/pPH1J1 |
| CP45 | iroN$_{ec}$:TnphoA | T4(CP9.45) x CP9 |
| CP9.82 | iron$_{ec}$:TnphoA, active TnphoA fusion | Kan$^R$exconjugant of CP9/pRT291 x MM294/pPH1J1 |
| CP82 | iroN$_{ec}$:TnphoA | T4(CP9.82) x CP9 |
| Plasmid | | |
| p45.1 | 21 kbSalI/SacI fragment from CP45 containing the leftward 5.0 kb of TnphoA (active fusion) and a portion of iroN$_{ec}$ cloned into pBS II SK (-) | |
| p45.3 | 22 kb ClaI/XbaI fragment from CP45 containing the rightward 6.7 kb of TnphoA (non-fusion) and a portion of iroN$_{ec}$ cloned into PBS II SK (-) | |
| p82.1 | 22 kb BamHI/SacI fragment from CF82 containing the leftward 5.0 kb of TnphoA (active fusion) and a portion of iron$_{ec}$ cloned into pBS II SK (-) | |

To establish that these mutants were isogenic derivatives of CP9, a series of studies were performed to exclude the possibility that cryptic mutations were acquired during the mutagenesis procedure.

Transduction of the transposon insertion back into the wild-type strain CP9 was accomplished using the bacteriophage T4 resulting in transductants CP45 and CP82. Whole cell DNA preparation, restriction enzyme (New England Biolabs, Beverly, Mass.) mediated DNA digestion and Southern hybridization using PCR generated radioactive probes was performed as described (Russo et al., 1993, supra). Primers 63 (SEQ ID NO:2) and 64 (SEQ ID NO:3) were used to amplify a 4.0 kb internal fragment of TnphoA (contained in pRT291), which were used to probe for TnphoA insertions. Southern analysis of Bgl II digested whole cell DNA containing TnphoA produces a 2.8 kb internal fragment and two variable junctions fragment per copy. Lipopolysaccharide (LPS), capsular polysaccharide, and outer membrane protein profiles were determined as described (Russo et al., 1995, Infec. Immun., 63:1263–1269).

In the mutants CP9.45 and CP9.82, and their respective T4 generated transductants, CP45 and CP82, it was established that the mutants had a single transposon insertion, that transduction of this insertion back into the wild type strain (CP9) resulted in a derivative that possessed the same degree of increased expression in urine relative to L-B medium as the original mutant, that in the transductants the transposon was physically in the same location as in the original mutant and that alterations in capsule, lipopolysaccharides and outer membrane profiles did not occur. This data establishes that CP45 and CP82 are isogenic derivatives of CP9 and that the gene into which TnphoA was inserted (iroN$_{ec}$) has increased expression in urine.

Subclones of the gene loci 5' to the TnphoA insertions in CP9.45(iroN$_{ec}$) were obtained by restricting whole cell DNA with BamHI or SalI, which recognizes a site located 3' to the kanamycin resistance gene in TnphoA plus SacI (CP45, CP82) which does not have restriction sites within TnphoA. Ligation of this restriction into pBSII SK(_), electroporation into XL1 Blue (Stratagene, Lajolla, Calif.) and selection of ampicillin (200 µg/ml) and kanamycin (40 µg/ml) resistant transformants resulted in the identification of the subclones p45.1 and p82.1 (Table 1). A subclone of the iroN$_{ec}$ gene locus 3' to the TnphoA insertion in CP9.45 was obtained by restricting whole cell DNA with ClaI which recognizes a site 5' to the kanamycin resistance gene in TnphoA and XbaI which does not possess a restriction site within TnphoA. Ligation of this restriction into pBSII SK(-), electroporation into XL1 Blue (Stratagene, Lajolla, Calif.), and selection of ampicillin and kanamycin resistant transformants resulted in the identification of the subclone p45.3.

DNA sequence was determined by the dideoxy chain termination method of Sanger (Sanger, et al, 1977, Proc. Natl. Acad. Sci. 85:5463–5467) using the gene subclones p45.1, p45.3 and p82.1 as the DNA templates. DNA sequencing of the gene subclones p45.1 and p82.1 initially utilized a TnphoA fusion joint primer (SEQ ID NO:4) which established the location for a given TnphoA insertion. Sequencing of the gene subclone p45.3 initially utilized the TnphoA primer (SEQ ID NO:5). Subsequent DNA sequence was determined using primers derived from the deduced sequences of the gene subclones. A consensus sequence for iroN$_{ec}$ was generated by assembling and editing the DNA sequence obtained from 34 overlapping but independent sequencing reactions using AssemblyLIGN 1.0.2 (Oxford Molecular Group, Beaverton, Oreg.). Both strands of the gene were sequenced. The sequence of iroN$_{ec}$ is disclosed in SEQ ID NO:1 (accession no. AF135597). Sequence analysis, comparisons, and CLUSTAL alignments were performed, in part, using MacVector (version 6.0, Oxford Molecular Group, Beaverton, Oreg.). Comparisons were also performed via BLAST analysis of the non-redundant GenBank+EMBL+DDBJ+PDB sequences. SignalP V1.1 was used for identification of signal sequences (Perez-Trallero et al., 1993, Eur. J. Clin. Microbiol. Infect. Dis., 12:349–351).

The DNA sequence indicates that this is a novel gene for *E. coli*. The predicted protein (IroN$_{ec}$) consists of 725 amino-acids (SEQ ID NO:8), a putative molecular weight of 79,380 kDa, an estimated pI of 5.68, and the first 24 a.a. represent a putative signal sequence. Comparison with entries in GenBank revealed that it was most homologous with iroN$_{se}$ (77% nucleotide homology), a recently identified catecholate siderophore receptor in *Salmonella enterica*. (Baumler, et al, 1998, 180:1446–1453). In *S. enterica*, iroN$_{se}$ is part of a five gene cluster that includes iroBCDEN. The specific functions of the gene products for iroBCDE remains unclear and a gene encoding the cognate siderophore for IroN$_{se}$ has yet to be identified. However, a putative Fur DNA binding site is present 5' to both iroN$_{se}$ (86 bases) and iroN$_{ec}$ (100 bases) with 15/19 bases conserved. Further, 184 bases 5' to the start site of iroN$_{ec}$ are 137 bases which were 87% (120/137) homologous to the Salmonella insertion sequence IS1230 (bases 1–137, accession no. AJ000635). These bases correspond to the first 137 bases from this IS3-like element, the first 39 of which consist of an imperfect inverted repeat.

(Collighan, et al, 1997, FEMS Micobiol. Lett. 154:207–213). This IS element was not present 5' to iroN$_{se}$. Taken together, this data suggests that iroN$_{ec}$ may have been acquired from *S. enterica* via IS-element mediated horizontal transfer. iroN$_{ec}$ possessed a lesser degree of homology with the catecholate siderophore receptors from *Pseudomonas aeruginosa* (pfeA), *Bordetella pertussis* (bfeA), and the fepA siderophore receptor from *E. coli*. The deduced protein sequence identity and similarity of IroN$_{ec}$ determined by pairwise amino acid alignment using the program CLUSTAL to IroN$_{se}$, FepA, PfeA, and BfeA is summarized in Table 2. Further, sequence analysis did not reveal any premature stop codons.

TABLE 2

Deduced protein sequence identity and similarity of IroN$_{ec}$ to IroN$_{se}$, FepA, and BfeA

|  | Homologue | % Identity | % Similarity |
|---|---|---|---|
| *Salmonella enterica* | IroN$_{ec}$ | 82% | 91% |
| *Escherichia coli* | FepA | 52% | 69% |
| *Pseudomonas aeruginosa* | PfeA | 52% | 69% |
| *Bordetella pertussis* | BfeA | 53% | 68% |

Additional sequence analysis of DNA 5' to iroN$_{ec}$ has demonstrated that this gene is 1.6 kb 3' to the prs gene cluster, which encodes the class III PapG adhesin (FIG. 1). Further, although the precise genomic organization of the region 5' to the prs operon has not been determined, the molecular usher for the F1C fimbria ((Klemm, et al, 1995, J. Bacteriol. 177:621–627) focD, has also been identified approximately 15.6 kb 5' to the deduced start site for iroN$_{ec}$ (FIG. 1). From left to right in FIG. 1 are shown: 11.8 kb sequence represented by the dotted line consists of the 5' portion of the iroD$_{ec}$ gene and genome 5' to it; a portion of the iroD$_{ec}$ gene (0.6 kb), iroE$_{ec}$ (0.9 kb) and iroN$_{ec}$(2.2 kb); a putative Fur binding site which is 100 bases 5' to the deduced start site of iroN$_{ec}$; a portion of an IS12230-like element (bp 1–137, accession number AJ000635) which is 184 bp 5' to the deduced start site of iroN$_{ec}$; and a 14 kb sequence represented by the dotted line (not to scale relative to solid line). The most distal boundary of this sequence consists of the 3' portion of focD, the molecular usher for the FIC fimbria. The arrow below the solid line indicate the direction of transcription.

EXAMPLE 2

This embodiment describes the phylogenetic distribution of iroN$_{ec}$ amongst various isolates of *E. coli*. A 667 base pair internal DNA probe (AF135597 bases 1729–2396) was generated from iroN$_{ec}$ which did not share any homology with fepA. This probe was used in a dot-blot assay as described below to detect for the presence of homologous iroN$_{ec}$ sequence.

DNA was prepared from relevant strains by boiling cells from overnight growth in L-B medium (1 ml concentrated to 200 μl of sterile H$_2$O) at 105° C. for 10 minutes. The supernatant was saved and used for analysis. Nytran membranes (Schleicher & Scheull, Keene, N.H.) were pre-wet in 6xSSC for 10 minutes and dotted with 3 μl of denatured DNA preparation from each strain in triplicate. The membrane was subsequently placed on filter paper saturated with denaturing solution (0.4N NaOH, 0.6M NaCl) followed by neutralizing solution (1.5M NaCl, 0.5M Tris HCl, pH 7) for 1 minute each, then air-dried, and UV cross-linked with 1200 Joules (UV Stratalinker 2400, Statagene, La Jolla, Calif.). Primers 192 (SEQ ID NO:6) and 197 (SEQ ID NO:7) were used to amplify a 0.67 kb internal fragment of iroN$_{ec}$ (contained in p45.3) that did not share any homology with fepA. Aqueous hybridization was performed under high stringency conditions (65° C.). Results were scored as either zero (no hybridization), 1[+], or 2[+]. Under these conditions the negative control strains (HB101, XL-1 Blue) were consistently scored as zero and the positive control strain CP9 as 2[+]. Experimental strains consisted of; Group 1: fourteen unique fecal isolates that had been previously established not to contain pap, hly, or cnf-1 (Johnson, et al, 1998, J. Infect. Dis. 177:1120–1124), Group 2: five unique fecal isolates that possessed some combination of pap, hly, or cnf-1, Group 3: twenty unique first-time UTI isolates (Russo, et al, 1995, J. Infect. Dis. 172:440–445), Group 4: fifteen unique recurrent UTI isolates (Russo, et al, 1995, J. Infect. Dis. 172:440–445), Group 5: twenty-one blood isolates obtained from patients hospitalized at Erie County Medical Center (Buffalo, N.Y.), Group 6: all 35 UTI isolates, and Group 7: all 56 clinical isolates. Group 1 was most representative of non-pathogenic or commensal strains and therefore was used in statistical comparisons against the clinical isolate Groups 5, 6, and 7. Fisher's exact test was used for the comparison of fecal versus clinical isolates for the presence of iroN$_{ec}$ DNA sequence via dot-blot assay.

The results from these studies are summarized in Table 3.

TABLE 3

Phylogenetic distribution of ironN$_{ec}$ homologous DNA sequence

| Dot-Blot Score | Group 1 | Group 2 | Group 3 | Group 4 | Group 5 | Group 6 | Group 7 |
|---|---|---|---|---|---|---|---|
| 0 | 43% | 20% | 5% | 7% | 10% | 6% | 7% |
| 1[+] | 43% | 0% | 50% | 27% | 57% | 40% | 46% |
| 2[+] | 14% | 80% | 45% | 67% | 33% | 54% | 46% |
| any → | 57% | 80% | 95% | 93% | 90% | 94% | 93% |

Dot-Blot Score: 0=no homology, 1[+]=positive homology, 2[+]=maximal homology, any[+]=the combination of 1[+] and 2[+]

Group 1: fourteen unique fecal isolates that had been previously established not to contain pap, hly, or cnf-1 and therefore are most representative of non-pathogenic strains.

Group 2: five unique fecal isolates that possessed some combination of pap, hly, or cnf-1 and therefore most likely represent pathogenic strains Group 3: twenty unique first-time UTI isolates Group 4: fifteen unique recurrent UTI isolates Group 5: twenty-one blood isolates obtained from patients hospitalized at Erie County Medical Center (Buffalo, N.Y.).

Group 6: All 35 UTI isolates (Groups 3 and 4).

Group 7: All 56 clinical isolates (Groups 3, 4 and 5).
[a]Fisher's exact test was used for proportions. All comparisons are versus Group 1. [b]P=0.039, [c]P=0.004, [d]P=0.003, [e]P=>0.10(NS), [f]P=0.01, [g]P=0.03

In summary, forty three percent of 14 fecal isolates (Group1, negative for pap, hly, or cnf1 and therefore most representative of non-pathogenic strains) did not possess DNA sequence homologous to iroN$_{ec}$. In contrast, only 20% of 5 fecal isolates (Group 2, positive for some combination of pap, hly, or cnf1 and therefore most likely pathogenic strains), 5% of 20 first-time UTI isolates (Group 3), 7% of 15 recurrent UTI isolates (Group 4), and 10% of 21 blood isolates (Group 5) were negative for iroN$_{ec}$ homologous sequence under high stringency conditions. The differences between Group 1 versus either Group 5, Group 6 (all UTI strains, Groups 3,4), or Group 7 (all clinical isolates, Groups 3,4,5) were statistically significant (P=0.039, P=0.004, P=0.003 respectively). In summary, this data demonstrates that DNA sequence homologous to iroN$_{ec}$ is significantly less prevalent in fecal isolates without the virulence genes pap, hly, or cnf1 than clinical isolates.

EXAMPLE 3

This embodiment describes the growth of CP9 and CP82 and the expression of iroN$_{ec}$ in human urine, human ascites and blood.

Ex Vivo Growth in Human Urine

Human urine from subjects who had and who never had experienced a UTI was used for studies assessing growth of strains ex vivo. The strain to be tested was grown overnight in 2 ml of L-B medium±kanamycin 40 µg/ml. The next day, the bacterial cells were diluted into urine to achieve a starting concentration of approximately $1.0 \times 10^{2-3}$ cfu/ml, since this titer is at the lower end of the spectrum for what is considered significant for UTI in symptomatic young women (Stamm, et al, 1982, N. Engl. J. Med. 307:463–468). For Å$_{600}$ growth curves, a starting Å$_{600}$ of about 0.03 was used. During incubation at 37° C., aliquots were removed at intervals and either the Å$_{600}$ was determined or the bacterial titers were established by plating 10-fold serial dilutions in 1×phosphate-buffered saline in duplicate on appropriate media.

Expression of IroN$_{ec}$ in Urine

Expression of iroN$_{ec}$ was increased in human urine relative to L-B. Since the composition of human urine has the potential to be variable, assays were performed using 17–29 independent urines collected from 10 different individuals. Five of these individuals were women with a prior history of UTIs. For CP9.82, the mean fold and median fold increase in expression of IroN$_{ec}$ was 27.2±5.0 and 19.0 respectively, the range being 2.4–132. Although there was variance in the degree of increased expression from urine to urine, increased expression was seen in all urines evaluated. The degree of expression of iroN$_{ec}$ was similar in urines from individuals with and without a prior history of UTI. The 17–29 independent urines used were filter sterilized and stored at 4° C. prior to use. To determine if the processing of urine affected gene expression, assays were performed in parallel using urines that were either 1) fresh and unfiltered, 2) fresh and filtered with a 0.22 micron filter, or 3) filtered and stored at 4° C. The expression of iroN$_{ec}$ was similar, regardless of how the urine was processed (data not shown).

Growth of CP9 (w.t.) and CP82 (iroN$_{ec}$) was evaluated in multiple independent urines via both enumeration of bacterial titers and Å$_{600}$. Growth of CP82 (5 urines) was equivalent to their wild-type parent CP9 (data not shown).

Expression of IroN$_{ec}$ in Human Ascites and Blood

The expression of various virulence traits may vary depending on the site of infection. Therefore iroN$_{ec}$, expression was evaluated in human blood and ascites, two additional body fluids which extraintestinal *E. coli* isolates commonly infect. To assess gene expression in human ascites and blood, filter sterilized ascites (peritoneal fluid) was obtained from a patient hospitalized at Erie County Medical Center, divided into multiple aliquots, and frozen at −80° C. Blood was used fresh and was obtained from a single donor. It was collected in sterile, 8.3 ml vacutainer tubes which contained 1.7 ml of sodium polyanetholesulfonate (0.35%) and NaCl (0.85%) (non-bactericidal) as the anti-coagulant. For blood assays the bacterial cells were washed×2 at 4° C. with 4 ml of 0.1M Tris (pH 9.8), 0.001M MgCl$_2$ buffer and resuspended in a total volume of 2 ml. For ascites assays the bacterial cells were concentrated via centrifugation and the resultant pellet was resuspended in 2 ml of 0.1M Tris (pH 9.8), 0.001M MgCl$_2$ buffer. Aliquots were removed×2 and cfu/ml were determined via serial 10-fold dilutions. Bacterial cells were subsequently permeabilized by adding 100 µl of 0.1% SDS and 200 µl of chloroform, vortexed×10 seconds and kept on ice. A fluorescent assay was performed because red blood cells±hemoglobin present in blood could not be reliably separated from bacterial cells. Their presence interfered with the colorimetric assays described above for measuring alkaline phosphatase activity. Assays were performed in a 48-well tissue culture plate. Each assay mixture consisted of 1 ml of Tris buffer, 50 µl of bacterial cell extract, and 50 µl (0.01M) of the fluorescent substrate (4-methylumbelliferonephosphate). Samples were read using a fluorescence multi-well plate reader (CytoFluor II, PerSeptive Biosystems, Framingham, Mass.) at an excitation setting of 360 nm, an emission setting of 460 nm, and a gain of 80 for 15 cycles. The net sample rate in blood or ascites relative to that in L-B broth established the fold induction. The net sample rate/ml (SR)={((fluorescence cycle B—fluorescence cycle A over the linear portion of the curve)/(elapsed time))×20}−(CP9 SR). Specific activities were determined by dividing net sample rates by cfu/ml. The sensitivity of the colorimetric and fluorescent assays was established to be similar.

The expression of iroN$_{ec}$ in blood and ascites was as follows. The mean fold increase in blood was 65.8±6.7 while the mean fold increase in ascites was 207±27. Although there was some variance in expression compared to urine, it should be noted that ascites and blood were obtained from single individuals.

EXAMPLE 4

This embodiment describes the regulation of the expression of iroN$_{ec}$ under various environmental conditions.

For osmoregulation studies, modified Davis medium was used with variable concentrations of either NaCl (0.05M–0.7M) or urea (0.05M–0.7M). Some gene regulation studies utilized urine to which exogenous Fe (0.1 mM) or glucose (0.5%) was added. M9 minimal medium was also utilized in gene regulation studies. Fe was chelated from M9 medium by mixing 200 ml of medium with 21.2 grams of washed (with 1L dH$_2$O×2) iminodiacetic acid (Chelex 100, Sigma, St. Louis, Mo.) for 90 minutes followed by filter sterilization. Siderophore production was determined using the Arnow assay as described (Schwyn, et al, 1987, Anal. Biochem. 160:47–56) and was concomitantly measured to confirm that the Fe concentration was limiting when chelated. As expected, siderophore production increased from 3.1 µM/Å$_{600}$ in the presence of Fe (0.1 mM) to 10.7 µM/Å$_{600}$ when Fe was chelated. The effect of pH on expression was determined using pooled urine whose pH was adjusted with either HCl or NaOH to achieve pHs of 5.0, 6.0, and 7.0. For a given experiment, assays were performed in triplicate and experiments were repeated at least once. Results were presented as the ratio of reporter gene expression in urine relative to L-B medium. For all of these studies quantitative alkaline phosphatase assays were performed as described above.

Iron: Sequence analysis of iroN$_{ec}$ strongly supports that this gene codes for a catecholate siderophore receptor, and therefore the role of Fe in the regulation of iroN$_{ec}$ was evaluated. Expression of iroN$_{ec}$ was measured when CP82 (iroN$_{ec}$) was grown in M9 minimal media in which Fe was either chelated or added exogenously. Compared to M9 medium plus Fe, iroN$_{ec}$ expression was increased 20.8-fold when CP82 was grown in Fe chelated M9 medium. Further, the addition of exogenous Fe to 3 independent human urines suppressed the increased expression of iroN$_{ec}$ relative to L-B medium (mean 64-fold decrease in phoA activity). These experimental findings, in combination with the identification of a Fur binding sequence 5' to the start of iroN$_{ec}$, suggest that iroN$_{ec}$ is Fur- regulated and that Fe is limited in urine.

pH: Although the pH of normal urine most commonly ranges from 5.5–6.5, values from 5.0 to 8.0 can occur. Therefore the effect of pH 5.0, 6.0, and 7.0 on the expression of iroN$_{ec}$ in human urine was evaluated. The expression of iroN$_{ec}$ was completely suppressed at pH 5.0 but unaffected at pH 6.0 and 7.0 with induction ratios of 0.23, 32, and 34 measured respectively. Therefore, urinary pH can affect gene expression of iroN$_{ec}$.

Thus, low Fe concentrations increase the expression of iroN$_{ec}$, and its expression is suppressed at a urinary pH 5.0, but unaffected by limiting concentrations of amino acids, nucleotides, or glucose.

EXAMPLE 5

This embodiment illustrates the use of the IroN$_{ec}$ for antigenic purposes. The entire protein encoded by iroN$_{ec}$ or antigenic fragments thereof can be used in vaccine formulations. Surface exposed epitopes of IroN$_{ec}$ can be identified by methods well known to those skilled in the art. For vaccine development, the IroN$_{ec}$ protein may be purified from the bacteria or may be purified from host containing a recombinant vector which expresses iroN$_{ec}$. The antigenic formulation may be introduced into the human or animal to be vaccinated by standard techniques well known to those skilled in the art.

To illustrate this embodiment, the IroN$_{ec}$ was purified following the cloning of the gene into an expression vector. The purified protein was used to elicit antibodies in mice. Immunized mice were challenged by the homologous strain of *E. coli* and protective abilities of this protocol determined. Cloning of the IroN$_{ec}$ For PCR-mediated amplification, the following 2 primers were designed for the entire iroN$_{ec}$ gene, excepting its signal sequence (2083 base pairs). These primers were derived from the iroN sequence (SEQ ID NO:1). The forward primer CGCGCGCGGATCCGACGAGACTCTGGTGGTGGA (SEQ ID NO:9) and the return primer CGCGCGCAAGCT-TGAATGATGCGGTAACTCCGG (SEQ ID NO:10) were used. A single band of the expected size was PCR amplified from CP9 chromosomal DNA. The DNA was cleaned and ligated into the Kanamycin resistant pet28a T7/his-tag expression vector. The pet28a::iroN construct was electroporated into XL1 Blue cells and selected for on LB plates containing Kanamycin. The iroN$_{ec}$ gene in the selected clone was confirmed to be correct by DNA sequencing. This excluded the possibility that an error was introduced into the cloned iroN$_{ec}$ during PCR amplification. The clone was subsequently electroporated into the expression cell line AD494 (DE3) pLysS for over-expression of IroN$_{ec}$.

Figure 2A:
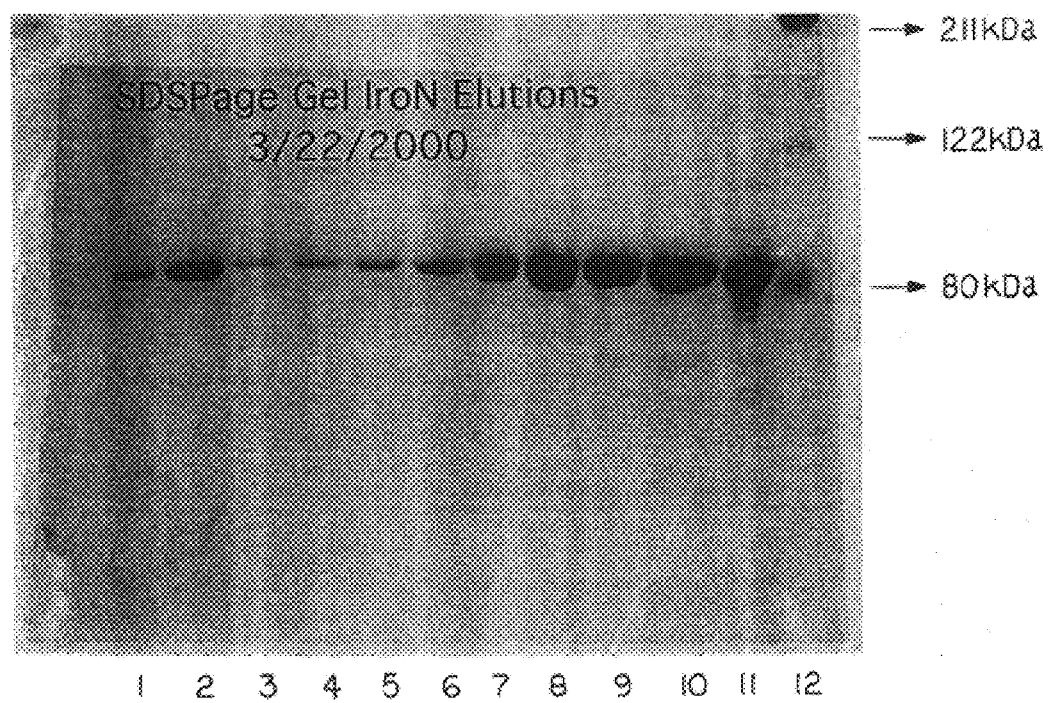
FIG. 2A is a representation of the SDS-PAGE analysis of IroN$_{ec}$ purification. Lane 12 represents molecular weight markers. The approximate molecular weight of each marker is indicated. Lane 11 is non-purified sample of the induced culture and lanes 1–10 are eluted IroN$_{ec}$.
Figure 2B:
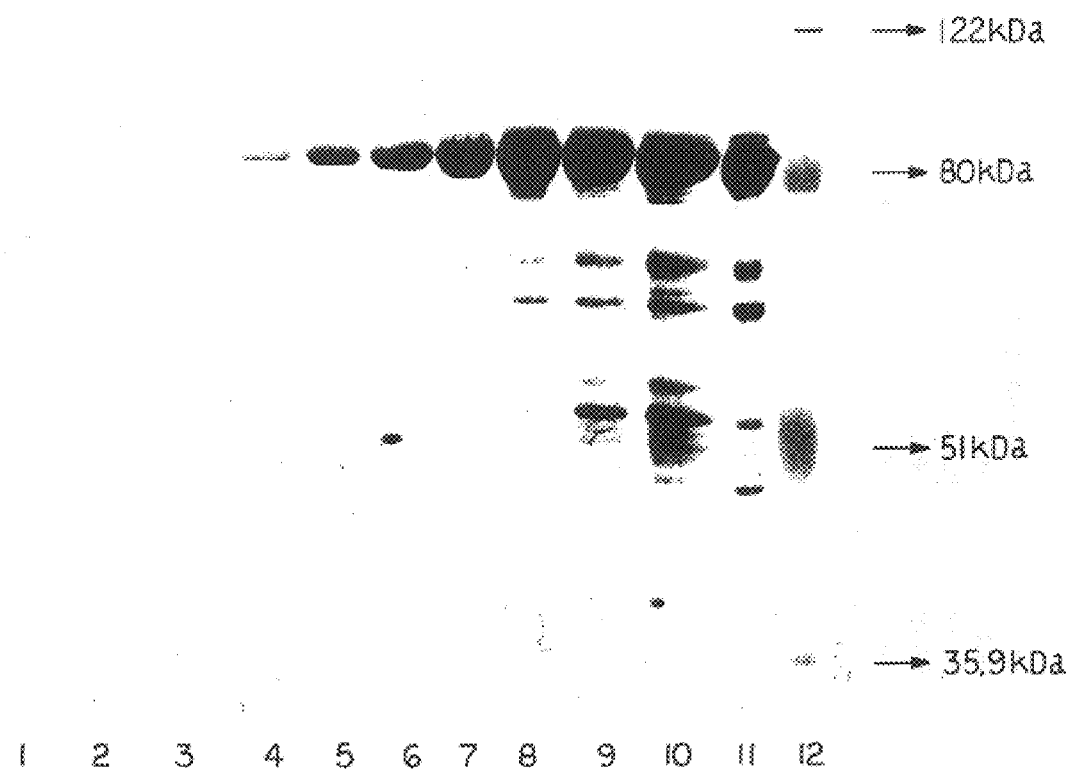
FIG. 2B is a representation of Western blot analysis of SDS-PAGE from FIG. 2A. An antibody to the recombinant IroN$_{ec}$ was used for detection. Lane 12 represents molecular weight markers having the indicated approximate molecular weights.

AD494 (DE3) pLysS::pet28a::iroN$_{ec}$ was grown overnight in LB media plus Kanamycin. The next morning, 1 ml of the overnight culture was transferred into 11 ml LB media plus Kanamycin and grown at 37° C. for 2.5 hours, shaking. IPTG was added to a final concentration of 1 mM to induce the expression of IroN$_{ec}$. One ml aliquots of the induced culture as well as an uninduced control culture were taken in 30 minute intervals. The samples were prepared for gel electrophoresis and run on a 7.5% SDS-PAGE gel (FIG. 2A). This figure shows the increased expression of IroN$_{ec}$ in the induced culture, migrating at approximately 80 kDa . This size is close to the deduced size of IroN$_{ec}$ (79.4 kDa) based on its DNA sequence. IroN$_{ec}$ was subsequently purified using TALON cobalt-based Immobilized Metal Affinity Chromatography and eluted under denaturing conditions using a 6M urea elution buffer at a pH between 5.1 and 5.3. A Western blot using the T7-Tag antibody specific to the recombinant protein was done. An intact IroN$_{ec}$ is represented by the primary band (FIG. 2B). The minor bands below IroN$_{ec}$ represent break-down products of IroN$_{ec}$ since these bands are all recognized by the T7-tag antibody which is specific to recombinant IroN$_{ec}$. This established that IroN$_{ec}$ was successfully purified. Purified IroN$_{ec}$ was stored at −20° C. until further use.

The successful expression of IroN$_{ec}$ confirmed that iroN$_{ec}$ encoded as a full length product. Further, the over-expressed and purified IroN$_{ec}$ was used as an immunogen in mice to determine if it was antigenic and elicited an antibody response.

Purified IroN$_{ec}$ Elicits a Strong Antibody Response in Mice

A putative vaccine candidate must be immunogenic. To establish that this is the case for IroN$_{ec}$, mice were immunized with purified IroN$_{ec}$ and sera pre and post-immunization were obtained and tested as follows.

a) Immunization protocol:

Balb C mice were used in an immunization protocol that was performed over a 5 week period. Mice were divided into 3 groups: Group 1, controls immunized with buffer only (N=15); Group 2, animals immunized with a total of 70 µg of IroN$_{ec}$ (N=12); and Group 3, animals immunized with a total of 150 µg of IroN$_{ec}$ (N=15) . Purified IroN$_{ec}$ was injected subcutaneously on days 1, 15 and 30 in a total of 200 µl for the first 2 immunizations and in 100 µl for the last immunization. No adjuvant was used. Sera were collected pre-immunization on day 1 and subsequently on days 22 and 36. The pre and post-immunization sera from these animals were evaluated by enzyme linked immunosorbent assay (ELISA) assay to assess for the development of antibodies directed against IroN$_{ec}$.

b) ELISA assay for detection of antibodies directed against IroN$_{ec}$:

ELISA assays were performed using Immulon 2 HB plates (DYNEX), coated with 75 ng of purified IroNec/well. The serum dilution was 1/1000. The conjugate used was Peroxidase-Labeled Goat anti Mouse IgG+IgM at a concentration of 1/10,000. IroN$_{ec}$ was adsorbed to the plate overnight. In the morning, the plate was washed and blocked using PIERCE Superbloc. After blocking, the plate was washed again and incubated with the diluted sera for 2 hours. The plate was washed again and incubated with the diluted conjugate for 1 hr before it was developed. Readings were measured at 450 nm on an automated ELISA plate reader.

The results of this assay are summarized in Table 4. As can be seen, a significant increase in antibodies directed against IroN$_{ec}$ developed in mice immunized with IroN$_{ec}$ (Groups 2 and 3) when compared with non-immunized controls (Group 1). Further, every animal in Group 2 and 3 had an antibody response of a similar magnitude. However, there was no difference in the magnitude of antibody response between the animals immunized with a total of 70 µg of IroN$_{ec}$ (Group 2) when compared to animals immunized with a total of 150 µg of IroN$_{ec}$ (Group 3). These results demonstrate that IroN$_{ec}$ is antigenic, a critical property of a vaccine candidate.

TABLE 4

Immunization with IroN$_{ec}$ elicits a strong antibody response in mice

| Immunizing regimen | ELISA OD$_{600}$ mean ± SEM | Post/Pre ratio |
|---|---|---|
| Controls | 0.043 ± 0.0007 (pre) 0.090 ± 0.010 (post) | 2.1 |
| Immunized with 70 µg of IroN$_{ec}$ | 0.084 ± 0.015 (pre) 1.31 ± 0.022 (post) | 15.6 |
| Immunized with 150 µg of IroN$_{ec}$ | 0.099 ± 0.008 (pre) 1.38 ± 0.015 (post) | 14.7 |

EXAMPLE 6

This embodiment demonstrates that immunization with IroN$_{ec}$ protects mice against challenge with the *Escherichia coli* strain CP9. Having established that immunization with IroN$_{ec}$ results in antibody production directed against IroN$_{ec}$, experiments were performed to evaluate whether this antibody response was protective against challenge with the homologous *E. coli* strain CP9. For initial studies an intra-peritoneal challenge model was used.

a) Intraperitoneal challenge model:

Both male and female mice (18–22 grams) underwent the immunizing regimen described above using purified IroN$_{ec}$ as the immunogen. The non-immunized control Group 1 consisted of 15 animals. Group 2 (N=12) and Group 3 (N=15) were immunized with a total of 70 µg and 150 µg of purified IroN$_{ec}$ respectively. Sera were obtained prior to and after immunization. Twelve days after the third and final immunizing dose of IroN$_{ec}$ was administered, animals underwent intra-peritoneal challenge with four different titers of the *E. coli* strain CP9. This infection model results in a systemic infection that may be lethal, depending on the magnitude of the challenge titer. For these experiments, challenge titers were utilized that would result in a 50–75% mortality rate in control animals. In this manner, a protective effect of immunization with IroN$_{ec}$ could be identified. The measured endpoints of this study were 1) death and 2) hepatic and splenic bacterial titers. Animals were observed post-bacterial challenge. Upon death, the liver and spleen were immediately removed, homogenized, and titered for bacterial counts via serial 10-fold dilutions. If an animal was still alive 18 hours after bacterial challenge it was sacrificed and bacterial titers of the liver and spleen were performed as described above. Since the antibody response against IroN$_{ec}$ was the same for Groups 2 and 3, these groups were pooled for the analysis presented below.

When antibody response was evaluated by ELISA, none of the control animals possessed significant pre-existing antibody to IroNec, nor did a significant antibody response occur after sham immunization. In contrast, all of the animals immunized with IroN$_{ec}$ developed a significant antibody response against it. The results are presented in Table 5.

TABLE 5

Immunization with IroN$_{ec}$ decreases mortality in mice challenged intraperitoneally with live *Escherichia coli* strain CP9

| Immunizing regimen | no. dead/no. Injected (%) | LD$_{50}$$^{\&}$ |
|---|---|---|
| Negative controls not immunized with IroN$_{ec}$ | | |
| 2.5 × 10$^6$ cfu$^{\#}$ | 1/3 (33) | 3.83 × 10$^6$ cfu |
| 8.1 × 10$^6$ | 3/4 (75) | |
| 2.5 × 10$^7$ | 4/4 (100) | |
| 8.1 × 10$^7$ | 4/4 (100) | |
| Immunized animals (immunized with IroN$_{ec}$) | | |
| 2.5 × 10$^6$ | 1/6 (16.6) | 7.84 × 10$^6$ cfu |
| 8.1 × 10$^6$ | 3/6 (50) | |
| 2.5 × 10$^7$ | 5/7 (71.4) | |
| 8.1 × 10$^7$ | 7/7 (100) | |

$^{\&}$= bacterial challenge dose needed for death in 50% of mice
$^{\#}$= bacterial colony forming units As shown in Table 5, immunization with IroN$_{ec}$ both resulted in a decreased mortality in immunized animals (higher LD$_{50}$ dose, 7.84×10$^6$ cfu) when compared to unimmunized controls (lower LD$_{50}$ dose, 3.83×10$^6$ cfu). Further, immunized control animals had diminished growth of CP9 in the liver and spleen when compared to unimmunized control animals (Table 6).

TABLE 6

Immunization with IroN$_{ec}$ diminishes bacterial growth in the liver and spleen of mice challenged intraperitoneally with live *Escherichia coli* strain CP9

| Immunizing regimen | Hepatic & Splenic growth/no. Injected (%) | GD$_{50}$$^{\&}$ |
|---|---|---|
| Negative controls (not immunized with IroN$_{ec}$) | | |
| 2.5 × 10$^6$ cfu$^{\#}$ | 1/3 (33) | 2.58 × 10$^6$ cfu |
| 8.1 × 10$^6$ | 4/4 (75) | |
| 2.5 × 10$^7$ | 4/4 (100) | |
| 8.1 × 10$^7$ | 4/4 (100) | |
| Immunized animals (immunized with IroN$_{ec}$) | | |
| 2.5 × 10$^6$ | 1/6 (16.6) | 7.84 × 10$^6$ cfu |
| 8.1 × 10$^6$ | 3/6 (50) | |
| 2.5 × 10$^7$ | 5/7 (71.4) | |
| 8.1 × 10$^7$ | 7/7 (100) | |

$^{\&}$= bacterial challenge dose needed for growth of CP9 in the liver and spleen of 50% of the mice
$^{\#}$= bacterial colony forming units In summary, immunization with purified IroN$_{ec}$ resulted in the development of antibodies directed against it. Further, these antibodies resulted in protection against subsequent bacterial challenge as shown by a diminished mortality rate and diminished growth of the model pathogen CP9 in liver and spleen.

From the foregoing, it will be obvious to those skilled in the art the various modifications in the above-described methods and compositions can be made without departing from the spirit and scope of the invention. Accordingly, the invention may be embodied in other specific forms without departing from the spirit or essential characteristics thereof. Present examples and embodiments, therefore, are to be considered in all respects as illustrative and not restrictive, and all changes which come within the meaning and range of equivalency of the specifications are therefore intended to be embraced therein.

What is claimed is:

1. An isolated polynucleotide consisting of a polynucleotide sequence selected from the group consisting of:
   (a) a polynucleotide sequence encoding a polypeptide of SEQ ID NO:8; and
   (b) a polynucleotide sequence which is complementary to the polynucleotide sequence of (a).

2. The isolated and purified polynucleotide of claim 1, wherein the polynucleotide consists of SEQ ID NO: 1.

3. A recombinant vector comprising the polynucleotide of claim 1.

4. A recombinant vector comprising the polynucleotide of claim 2.

5. A host cell comprising the recombinant vector of claim 3.

6. A host cell comprising the recombinant vector of claim 4.

* * * * *

UNITED STATES PATENT AND TRADEMARK OFFICE
CERTIFICATE OF CORRECTION

PATENT NO. : 6,410,703 B1
DATED : June 25, 2002
INVENTOR(S) : Russo et al.

It is certified that error appears in the above-identified patent and that said Letters Patent is hereby corrected as shown below:

<u>Column 1,</u>
Line 4, please insert -- This invention was made with Government support under Grant No. AI 42059 awarded by the National Institutes of Health. The Government has certain rights in the invention --.

Signed and Sealed this

Sixteenth Day of September, 2003

JAMES E. ROGAN
*Director of the United States Patent and Trademark Office*

SEQUENCE LISTING

<160> NUMBER OF SEQ ID NOS: 10

<210> SEQ ID NO 1
<211> LENGTH: 2495
<212> TYPE: DNA
<213> ORGANISM: Escherichia coli
<220> FEATURE:

<400> SEQUENCE: 1

| | | | | |
|---|---|---|---|---|
| ctctgactcg | cccgtcacga | ctggaatcat | gaaggcgttc aagttcagct | 50 |
| ttttgttgct | cagtaatgaa | tattttcatg | ttggacagca tgatcttctg | 100 |
| ttgctgaaaa | atcaagcatc | ttcaatgatc | acgggtatat atcaatttga | 150 |
| tatttatgaa | aaatcaatag | atttatcttg | tgagggattg cttttctttt | 200 |
| tgctaaatga | tattaattat | cattcttata | taaaaacaat aatggcagta | 250 |
| agaaatatct | ggcaaggatg | tgagcttaac | gatcaaacat tttaagttag | 300 |
| gcatttatta | gggaatagga | atgagaatta | acaaaatcct ctggtcgcta | 350 |
| actgtgctcc | tagttgggtt | gaatagccag | gtatcagtag ccaaatactc | 400 |
| cgacgatgat | aatgacgaga | ctctggtggt | ggaagccacc gctgagcagg | 450 |
| tattaaaaca | gcagccgggc | gtgtcggtta | ttaccagcga ggatattaaa | 500 |
| aagacccctc | cggtaaacga | cctttcagat | attattcgta aaatgcctgg | 550 |
| tgttaatctt | accggcaata | gcgcctcggg | cacacgcggt aataaccgcc | 600 |
| agatcgatat | tcgtggtatg | gggccggaaa | acaccttaat tttaattgat | 650 |
| ggtgtaccgg | tgacgtcacg | taactccgtg | cgttatagct ggcgtgggga | 700 |
| gcgtgatacc | cgcggtgaca | ccaactgggt | gccaccggaa caggttgagc | 750 |
| gtattgaagt | gatccgcggc | cctgcggcgg | cgcgctacgt tcgggggcc | 800 |
| gccgggggg | tggtgaacat | cattaccaaa | cgtcccacca acgactggca | 850 |
| cggttcgctg | tcgttataca | ccaaccagcc | ggaaagtagc gaagagggcg | 900 |
| ctacgcgtcg | cgccaatttc | agccttagtg | ggcctctggc tggtgatgct | 950 |
| cttaccacgc | gtttgtatgg | taacctgaat | aaaacggatg ctgacagttg | 1000 |
| ggatattaat | tctccggtcg | gtacgaaaaa | cgcagccggg catgaagggg | 1050 |
| tacgtaacaa | agatattaac | ggcgttgtct | cgtggaaatt aaatccgcag | 1100 |
| cagattctcg | atttcgaagt | cggatatagc | cgccagggga atatctatgc | 1150 |
| gggcgatacg | cagaacagtt | cttccagtgc | agttaccgaa agcctggcaa | 1200 |
| aatccggcaa | agagacgaac | cgcctgtacc | gacagaatta tggcattacg | 1250 |
| cataatggta | tctgggactg | gggacaaagt | cgctttggtg tttattacga | 1300 |
| gaaaccaat | aatacccgca | tgaatgaagg | attatccggc ggtggtgaag | 1350 |
| gacgtatttt | agcgggtgaa | aagtttacga | ccaatcgcct gagttcctgg | 1400 |
| cgaaccagcg | gtgagcttaa | tattcctttg | aatgtgatgg ttgatcaaac | 1450 |
| gctgaccgtt | ggtgcagagt | ggaaccgcga | taagctcgat gatccttcct | 1500 |

-continued

| | |
|---|---|
| ctaccagcct gacggtgaat gacagagata tcagcggtat ttctggctct | 1550 |
| gctgcggatc gcagcagtaa aaatcattct caaatcagtg cgctgtatat | 1600 |
| tgaagataac attgagccgg ttcctggcac gaatatcatt cccggcctgc | 1650 |
| gctttgatta tctcagcgac tccggcggga acttcagccc cagtctgaat | 1700 |
| ctttcgcagg aattgggcga ttatttcaaa gtcaaagcag gggttgcccg | 1750 |
| aacctttaaa gccccaaacc tgtatcaatc cagtgaaggc tatctgctct | 1800 |
| actcgaaagg caatggctgt ccaaaagata ttacatcagg cgggtgctac | 1850 |
| ctgatcggta ataaagatct cgatccggaa atcagcgtca ataaagaaat | 1900 |
| tggactggag ttcacctggg aagattacca cgcaagtgtg acctacttcc | 1950 |
| gcaatgatta ccagaataag atcgtggccg gggataacgt tatcgggcaa | 2000 |
| accgcttcag gcgcatatat cctcaagtgg cagaatggcg ggaaagctct | 2050 |
| ggtggacggt atcgaagcca gtatgtcttt cccactggtg aaagagcgtc | 2100 |
| tgaactggaa taccaatgcc acatggatga tcacttcgga gcaaaaagac | 2150 |
| accggtaatc ctctgtcggt catcccgaaa tatactatca ataactcgct | 2200 |
| taactggacc atcacccagg cgttttctgc cagcttcaac tggacgttat | 2250 |
| atggcagaca aaaaccgcgt actcatgcgg aaacccgcag tgaagatact | 2300 |
| ggcggtctgt caggtaaaga gctgggcgct tattcactgg tggggacgaa | 2350 |
| cttcaattac gatattaata aaaatctgcg tcttaatgtc ggcgtcagta | 2400 |
| atatcctcaa taaacagatc ttccgatctt ctgaaggggc gaataccgat | 2450 |
| aacgagccag gccgggctta ttatgccgga gttaccgcat cattc | 2495 |

<210> SEQ ID NO 2
<211> LENGTH: 18
<212> TYPE: DNA
<213> ORGANISM: artificial sequence
<220> FEATURE:
<223> OTHER INFORMATION: completely synthesized primer

<400> SEQUENCE: 2
gatcaagaga caggatga                                           18

<210> SEQ ID NO 3
<211> LENGTH: 18
<212> TYPE: DNA
<213> ORGANISM: artificial sequence
<220> FEATURE:
<223> OTHER INFORMATION: completely synthesized primer

<400> SEQUENCE: 3
tgatcctcgc cgtactgc                                           18

<210> SEQ ID NO 4
<211> LENGTH: 15
<212> TYPE: DNA
<213> ORGANISM: artificial sequence
<220> FEATURE:
<223> OTHER INFORMATION: completely synthesized primer

<400> SEQUENCE: 4
aatatcgccc tgagc                                              15

<210> SEQ ID NO 5
<211> LENGTH: 18

-continued

```
<212> TYPE: DNA
<213> ORGANISM: artificial sequence
<220> FEATURE:
<223> OTHER INFORMATION: completely synthesized primer

<400> SEQUENCE: 5
catgttagga ggtcacat                                                    18

<210> SEQ ID NO 6
<211> LENGTH: 18
<212> TYPE: DNA
<213> ORGANISM: artificial sequence
<220> FEATURE:
<223> OTHER INFORMATION: completely synthesized primer

<400> SEQUENCE: 6
gacgccgaca ttaagacg                                                    18

<210> SEQ ID NO 7
<211> LENGTH: 19
<212> TYPE: DNA
<213> ORGANISM: artificial sequence
<220> FEATURE:
<223> OTHER INFORMATION: completely synthesized primer

<400> SEQUENCE: 7
aagtcaaagc agggttgc                                                    19

<210> SEQ ID NO 8
<211> LENGTH: 725
<212> TYPE: PRT
<213> ORGANISM: Escherichia coli
<220> FEATURE:

<400> SEQUENCE: 8

Met Arg Ile Asn Lys Ile Leu Trp Ser Leu Thr Val Leu Leu Val
 1               5                  10                  15

Gly Leu Asn Ser Gln Val Ser Val Ala Lys Tyr Ser Asp Asp Asp
                20                  25                  30

Asn Asp Glu Thr Leu Val Val Glu Ala Thr Ala Glu Gln Val Leu
                35                  40                  45

Lys Gln Gln Pro Gly Val Ser Val Ile Thr Ser Glu Asp Ile Lys
                50                  55                  60

Lys Thr Pro Pro Val Asn Asp Leu Ser Asp Ile Ile Arg Lys Met
                65                  70                  75

Pro Gly Val Asn Leu Thr Gly Asn Ser Ala Ser Gly Thr Arg Gly
                80                  85                  90

Asn Asn Arg Gln Ile Asp Ile Arg Gly Met Gly Pro Glu Asn Thr
                95                  100                 105

Leu Ile Leu Ile Asp Gly Val Pro Val Thr Ser Arg Asn Ser Val
                110                 115                 120

Tyr Ser Trp Arg Gly Glu Arg Asp Thr Arg Gly Asp Thr Asn Arg
                125                 130                 135

Trp Val Pro Pro Glu Gln Val Glu Arg Ile Glu Val Ile Arg Gly
                140                 145                 150

Pro Ala Ala Ala Arg Tyr Gly Ser Gly Ala Ala Gly Gly Val Val
                155                 160                 165

Asn Ile Ile Thr Lys Arg Pro Thr Asn Asp Trp His Gly Ser Leu
                170                 175                 180

Ser Leu Tyr Thr Asn Gln Pro Glu Ser Ser Glu Glu Gly Ala Thr
```

-continued

```
                185                 190                 195
Arg Arg Ala Asn Phe Ser Leu Ser Gly Pro Leu Ala Gly Asp Ala
                200                 205                 210

Leu Thr Thr Arg Leu Tyr Gly Asn Leu Asn Lys Thr Asp Ala Asp
                215                 220                 225

Ser Trp Asp Ile Asn Ser Pro Val Gly Thr Lys Asn Ala Ala Gly
                230                 235                 240

His Glu Gly Val Arg Asn Lys Asp Ile Asn Gly Val Val Ser Trp
                245                 250                 255

Lys Leu Asn Pro Gln Gln Ile Leu Asp Phe Glu Val Gly Tyr Ser
                260                 265                 270

Arg Gln Gly Asn Ile Tyr Ala Gly Asp Thr Gln Asn Ser Ser Ser
                275                 280                 285

Ser Ala Val Thr Glu Ser Leu Ala Lys Ser Gly Lys Glu Thr Asn
                290                 295                 300

Arg Leu Tyr Arg Gln Asn Tyr Gly Ile Thr His Asn Gly Ile Trp
                305                 310                 315

Asp Trp Gly Gln Ser Arg Phe Gly Val Tyr Tyr Glu Lys Thr Asn
                320                 325                 330

Asn Thr Arg Met Asn Glu Gly Leu Ser Gly Gly Glu Gly Arg
                335                 340                 345

Ile Leu Ala Gly Glu Lys Phe Thr Thr Asn Arg Leu Ser Ser Trp
                350                 355                 360

Arg Thr Ser Gly Glu Leu Asn Ile Pro Leu Asn Val Met Val Asp
                365                 370                 375

Gln Thr Leu Thr Val Gly Ala Glu Trp Asn Arg Asp Lys Leu Asp
                380                 385                 390

Asp Pro Ser Ser Thr Ser Leu Thr Val Asn Asp Arg Asp Ile Ser
                395                 400                 405

Gly Ile Ser Gly Ser Ala Ala Asp Arg Ser Ser Lys Asn His Ser
                410                 415                 420

Gln Ile Ser Ala Leu Tyr Ile Glu Asp Asn Ile Glu Pro Val Pro
                425                 430                 435

Gly Thr Asn Ile Ile Pro Gly Leu Arg Phe Asp Tyr Leu Ser Asp
                440                 445                 450

Ser Gly Gly Asn Phe Ser Pro Ser Leu Asn Leu Ser Gln Glu Leu
                455                 460                 465

Gly Asp Tyr Phe Lys Val Lys Ala Gly Val Ala Arg Thr Phe Lys
                470                 475                 480

Ala Pro Asn Leu Tyr Gln Ser Ser Glu Gly Tyr Leu Leu Tyr Ser
                485                 490                 495

Lys Gly Asn Gly Cys Pro Lys Asp Ile Thr Ser Gly Gly Cys Tyr
                500                 505                 510

Leu Ile Gly Asn Lys Asp Leu Asp Pro Glu Ile Ser Val Asn Lys
                515                 520                 525

Glu Ile Gly Leu Glu Phe Thr Trp Glu Asp Tyr His Ala Ser Val
                530                 535                 540

Thr Tyr Phe Arg Asn Asp Tyr Gln Asn Lys Ile Val Ala Gly Asp
                545                 550                 555

Asn Val Ile Gly Gln Thr Ala Ser Gly Ala Tyr Ile Leu Lys Trp
                560                 565                 570

Gln Asn Gly Gly Lys Ala Leu Val Asp Gly Ile Glu Ala Ser Met
                575                 580                 585
```

```
Ser Phe Pro Leu Val Lys Glu Arg Leu Asn Trp Asn Thr Asn Ala
                590                 595                 600

Thr Trp Met Ile Thr Ser Glu Gln Lys Asp Thr Gly Asn Pro Leu
                605                 610                 615

Ser Val Ile Pro Lys Tyr Thr Ile Asn Asn Ser Leu Asn Trp Thr
                620                 625                 630

Ile Thr Gln Ala Phe Ser Ala Ser Phe Asn Trp Thr Leu Tyr Gly
                635                 640                 645

Arg Gln Lys Pro Arg Thr His Ala Glu Thr Arg Ser Glu Asp Thr
                650                 655                 660

Gly Gly Leu Ser Gly Lys Glu Leu Gly Ala Tyr Ser Leu Val Gly
                665                 670                 675

Thr Asn Phe Asn Tyr Asp Ile Asn Lys Asn Leu Arg Leu Asn Val
                680                 685                 690

Gly Val Ser Asn Ile Leu Asn Lys Gln Ile Phe Arg Ser Ser Glu
                695                 700                 705

Gly Ala Asn Thr Tyr Asn Glu Pro Gly Arg Ala Tyr Tyr Ala Gly
                710                 715                 720

Val Thr Ala Ser Phe
                725

<210> SEQ ID NO 9
<211> LENGTH: 33
<212> TYPE: DNA
<213> ORGANISM: Artificial Sequence
<220> FEATURE:
<223> OTHER INFORMATION: forward primer for PCR

<400> SEQUENCE: 9
cgcgcgcgga tccgacgaga ctctggtggt gga                                    33

<210> SEQ ID NO 10
<211> LENGTH: 33
<212> TYPE: DNA
<213> ORGANISM: Artificial Sequence
<220> FEATURE:
<223> OTHER INFORMATION: reverse primer for PCR

<400> SEQUENCE: 10
cgcgcgcaag cttgaatgat gcggtaactc cgg                                    33
```